(12) United States Patent
Kobe et al.

(10) Patent No.: US 11,951,226 B2
(45) Date of Patent: Apr. 9, 2024

(54) ETHYLENE OXIDE STERILIZATION SENSOR INCLUDING ACID-FUNCTIONAL SORBENT AND METHOD OF USE

(71) Applicant: 3M INNOVATIVE PROPERTIES COMPANY, St. Paul, MN (US)

(72) Inventors: Michael W. Kobe, Lake Elmo, MN (US); Michael S. Wendland, North St. Paul, MN (US); Kelvin J. Witcher, Hudson, WI (US); Richard C. Webb, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 558 days.

(21) Appl. No.: 16/949,727

(22) Filed: Nov. 12, 2020

(65) Prior Publication Data

US 2021/0154347 A1    May 27, 2021

Related U.S. Application Data

(60) Provisional application No. 62/939,913, filed on Nov. 25, 2019.

(51) Int. Cl.
| | |
|---|---|
| A61L 2/28 | (2006.01) |
| A61L 2/20 | (2006.01) |
| G01N 21/77 | (2006.01) |
| A61L 101/44 | (2006.01) |

(52) U.S. Cl.
CPC ............... A61L 2/28 (2013.01); A61L 2/206 (2013.01); G01N 21/77 (2013.01); A61L 2101/44 (2020.08)

(58) Field of Classification Search
CPC ........ A61L 2/28; A61L 2/206; A61L 2101/44; G01N 21/77
See application file for complete search history.

(56) References Cited

U.S. PATENT DOCUMENTS

| | | | |
|---|---|---|---|
| 3,531,463 | A | 9/1970 | Gustafson |
| 4,138,216 | A | 2/1979 | Larsson |
| 4,436,858 | A | 3/1984 | Klosiewicz |
| 4,448,548 | A | 5/1984 | Foley |
| D315,600 | S | 3/1991 | Niven |
| 5,145,935 | A | 9/1992 | Hayashi |
| 5,155,199 | A | 10/1992 | Hayashi |
| RE34,515 | E | 1/1994 | Foley |
| 5,378,430 | A | 1/1995 | Nieves |
| 5,451,372 | A * | 9/1995 | Larsson ................. A61L 2/206 431/1 |

(Continued)

FOREIGN PATENT DOCUMENTS

WO    WO 2017-106434    6/2017

OTHER PUBLICATIONS

Wikipedia, "Phosphoric Acid" (Year: 2023).*

(Continued)

*Primary Examiner* — Sean E Conley
*Assistant Examiner* — Brendan A Hensel (57) ABSTRACT

An ethylene oxide sterilization sensor, and method of use, wherein the sensor includes: a heat-shrinkable film; an acid-functional porous sorbent in thermal contact with the heat-shrinkable film; and an acid having a boiling point above 120° C. and a pKa of no greater than 2.5, wherein the acid is impregnated in or covalently attached to the porous sorbent.

12 Claims, 4 Drawing Sheets

(56) References Cited

U.S. PATENT DOCUMENTS

| | | | |
|---|---|---|---|
| 5,506,300 | A | 4/1996 | Ward |
| 5,665,822 | A | 9/1997 | Bitler |
| 6,160,084 | A | 2/2000 | Langer |
| 6,388,043 | B1 | 5/2002 | Langer |
| 6,416,487 | B1 | 7/2002 | Braverman |
| 6,423,421 | B1 | 7/2002 | Banaszak |
| 7,173,096 | B2 | 2/2007 | Mather |
| 7,893,179 | B2 | 2/2011 | Anderson |
| 9,134,251 | B2 | 9/2015 | Thomas |
| 2005/0244353 | A1 | 11/2005 | Lendlein |
| 2006/0041089 | A1 | 2/2006 | Mather |
| 2007/0009465 | A1 | 1/2007 | Lendlein |
| 2007/0282181 | A1 | 12/2007 | Findlay |
| 2010/0043694 | A1* | 2/2010 | Patel ............... G09F 3/0341 156/60 |
| 2014/0154808 | A1* | 6/2014 | Patel ............... A61L 2/206 436/1 |
| 2019/0212311 | A1* | 7/2019 | Hammond ............ G01N 21/80 |
| 2021/0114356 | A1* | 4/2021 | Wynne ............... B32B 27/302 |

OTHER PUBLICATIONS

Cotton Morphology and Cellulose Chemistry (Year: 2023).*
Ahn, "Rapid Generation and Control of Microporosity, Bimodal Pore Size Distribution, and Surface Area in Davankov-Type Hyper-Cross-Linked Resins", Macromolecules, 2006, vol. 39, pp. 627-632.
Davankov, "Structure and properties of hypercrosslinked polystyrene—the first representative of a new class of polymer networks", Reactive Polymers, 1990, vol. 13, pp. 27-42.
Hussein, "New Technologies for Active Disassembly: Using the Shape Memory Effect in Engineering Polymers", Int. J. Product Development, 2008, vol. 6, pp. 431-449.
Li, "A New Strategy to Microporous Polymers: Knitting Rigid Aromatic Building Blocks by External Cross-Linker", Macromolecules, 2011, vol. 44, pp. 2410-2414.
Liu, "Unexpected Behavior of 1-Chlorodecane as a Novel Porogen in the Preparation of High-Porosity Poly(divinylbenzene) Microspheres", J. Phys. Chem. C, 2008, vol. 112, pp. 13171-13174.
Mohamed, "Porous copolymer resins: Tuning pore structure and surface area with non-reactive porogens", Nanomaterials, 2012, vol. 2, pp. 163-186.
Nyhus, Formation of the porous structure during the polymerization of meta-Divinylbenzene and para-Divinylbenzene with Toluene and 2-Ethylhexanoic Acid (2-EHA) as Porogens, J. Poly. Sci. Part A: Polymer Chemistry, 1999, vol. 37, pp. 3973-3990.
Wei, "Solvothermal synthesis of highly porous polymers and their controllable transition from macro/mesoporosity to meso/microporosity", Colloids and Surfaces A: Physiochem. Eng. Aspects, 2012, vol. 414, pp. 327-332.
Wood, "Hydrogen Storage in Microporous Hypercrosslinked Organic Polymer Networks", Chem. Mater., 2007, vol. 19, pp. 2034-2048.
Zhang, "Superhydrophobic nanoporous polymers as efficient adsorbents for organic compounds", Nano Today, 2009, vol. 4, pp. 135-142.

* cited by examiner

ETHYLENE OXIDE STERILIZATION SENSOR INCLUDING ACID-FUNCTIONAL SORBENT AND METHOD OF USE

CROSS REFERENCE TO RELATED APPLICATION

This application claims the benefit of U.S. Provisional Patent Application No. 62/939,913, filed Nov. 25, 2019, the disclosure of which is incorporated by reference herein in its entirety.

BACKGROUND

Ethylene oxide (EO) is one of four typical forms of sterilization along with steam, hydrogen peroxide, and ultraviolet (UV). Ethylene oxide (EO) is used at low temperatures to sterilize temperature sensitive materials and equipment. EO sterilization is usually performed in a sealed chamber. Often, such chamber is packed with materials and equipment during the sterilization process. Packing the chamber to its maximum capacity to have the highest rate of turnover for materials needing to be sterilized occurs because the whole process can take quite a while, in some cases a whole day. The time-consuming step in the EO sterilization process is the aeration of the chamber where the EO is completely flushed out with air. Due to electrical constraints with the design of the chamber, only Venturi pumps can be used during the chamber flush, which tend to be relatively low flowing, hence the long aeration time.

With the chamber typically being filled to capacity during the sterilization process, it is not uncommon for areas in the chamber to never see full exposure to EO resulting in some items not being properly sterilized. It is important then to have sensors scattered throughout the chamber that can be analyzed to ensure that proper and complete sterilization occurred everywhere. These sensors can be indicators, which indicate that one process condition has been met, or integrators, which indicate two or more process conditions have been met.

Process conditions include EO concentration, time, relative humidity (RH), and pressure. The most reliable method of sterilization indication is using biological indicators. In this method, tubes containing spores are placed in various locations throughout the chamber. Upon completion of the sterilization cycle, the tubes are collected from the chamber and analyzed to ensure that the spores have been killed. It can be common for dozens of tubes to be used for each cycle. Analysis of each tube takes at least 24 minutes to complete, so it can take hours after a cycle is complete to ensure proper sterilization occurred. The biological indicators are also more expensive compared to other indicators.

Another common and relatively cheap sterilization sensor is colorimetric, which usually is in the form of a sticker printed with a dye. Upon exposure to EO, the sticker transitions from one color to another. While seemingly a simple idea, use of color to determine sterilization can be very subjective as one individual's perception of color or degree of color will vary from person to person. Thus, a more objective indicator at the same relatively cheap cost is desired.

SUMMARY OF THE DISCLOSURE

The present disclosure provides ethylene oxide sterilization sensors that include acid-functional sorbents and heat-shrinkable films.

In certain embodiments, the sensor includes: a heat-shrinkable film; an acid-functional porous sorbent in thermal contact (which may or may not be direct physical contact) with the heat-shrinkable film; and an acid having a boiling point above 120° C. and a pKa of no greater than 2.5, wherein the acid is impregnated in or covalently attached to the porous sorbent.

In this context, an "acid" includes acid compounds as well as acid moieties. Examples of acid compounds include sulfuric acid, phosphoric acid, alkyl sulfonic acid, alkyl phosphonic acid, benzene sulfonic acid, and toluene sulfonic acid. In this context, "alkyl" refers to C1-C4 alkyl groups, with methyl and ethyl being preferred. Examples of acid moieties include sulfonic acid ($—SO_3H$) and phosphonic acid ($—PO_3H_2$) groups.

This sensor utilizes an exothermic interaction between ethylene oxide and the acid in contact with the porous (high surface area) sorbent. The heat generated from the interaction, which can be both catalytic and reactive, causes a dimensional change in the heat-shrinkable film. The shrinkage of the heat-shrinkable film, as a result of this activation by ethylene oxide, is what indicates proper sterilization.

The present disclosure also provides a method of detecting ethylene oxide in a sterilization process, the method comprising: providing an ethylene oxide sterilization sensor comprising: a heat-shrinkable film; an acid-functional porous sorbent in thermal contact with the heat-shrinkable film; and an acid having a boiling point above 120° C. and a pKa of no greater than 2.5, wherein the acid is impregnated in or covalently attached to the porous sorbent; allowing ethylene oxide to contact the acid in contact with the porous sorbent to generate thermal energy sufficient to shrink the heat-shrinkable film; and detecting completion of the ethylene oxide sterilization process.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

In this application, terms such as "a," "an," and "the" are not intended to refer to only a singular entity but include the general class of which a specific example may be used for illustration. The terms "a," "an," and "the" are used interchangeably with the phrases "at least one" and "one or more." The phrases "at least one of" and "comprises at least one of" followed by a list refers to any one of the items in the list and any combination of two or more items in the list.

The term "or" is generally employed in its usual sense including "and/or" unless the content clearly dictates otherwise.

The term "and/or" means one or all the listed elements or a combination of any two or more of the listed elements.

Also, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also, the recitations of numerical ranges by endpoints include all numbers subsumed within that range as well as the endpoints (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

BRIEF DESCRIPTION OF THE FIGURES

FIG. 1 is a top view of one embodiment of an EO sterilization sensor of the present disclosure, wherein

FIG. 2 is a cross-section of the EO sterilization sensor of FIG. 1a.

FIG. 3 is a top view of an alternative embodiment of an EO sterilization sensor of the present disclosure, wherein

FIG. 4 is a cross-section of the EO sterilization sensor of FIG. 3a.

FIG. 6 is a representation of the EO sterilization sensor of FIG. 5 before activation by ethylene oxide, wherein FIG. 6a represents a top view and FIG. 6b a cross-sectional view.

FIG. 7 is a representation of the EO sterilization sensor of FIG. 5 after activation by ethylene oxide, wherein

DETAILED DESCRIPTION OF ILLUSTRATIVE EMBODIMENTS

The present disclosure provides an ethylene oxide (EO) sterilization sensor that includes an acid-functional sorbent and a heat-shrinkable film.

In certain embodiments, the sensor includes: a heat-shrinkable film; an acid-functional porous sorbent in thermal contact with the heat-shrinkable film; and an acid having a boiling point above 120° C. and a pKa of no greater than 2.5, wherein the acid is impregnated in or covalently attached to the porous sorbent. In certain embodiments, the acid-functional porous sorbent is adhered to the heat-shrinkable film using a layer of an adhesive. Multiple such sensors can be incorporated into an array if desired.

This sensor involves an EO process indicator that utilizes an exothermic interaction between ethylene oxide and the acid in contact with the porous (high surface area) sorbent. The heat generated from the interaction, which can be both catalytic and reactive, causes a dimensional change (i.e., shrinkage) in the heat-shrinkable film. The degree of shrinkage in the film will depend on the amount of heat to which it is exposed, which is a function of how much EO it "sees."

The shrinkage of the heat-shrinkable film provides a visual indicator. For example, the original dimensions of the film can simply be noted by an outline around it. Shrinkage of the film results in revealing of the outline. Alternatively, or additionally, shrinkage of the film can reveal an underlying picture, word, colored feature, or differently colored backing substrate.

The sensors of the present disclosure can be tailored by several factors in the construction of the sensor. Such factors include, for example, the sorbent loading in terms of grams sorbent per square meter of heat-shrinkable film, the identity of the acid, the concentration of acid in terms of millimoles per gram or weight percent per gram of acid-functional porous sorbent, and the type of heat-shrinkable film. When the acid-functional porous sorbent is adhered to the heat-shrinkable film using a layer of an adhesive, the layer of adhesive can function as a buffer or insulator. Thus, the thickness of the adhesive can be tailored to control the level of shrinkage.

In certain embodiments, the acid-functional porous sorbent is encapsulated. To keep the acid-functional porous sorbent encapsulated, it may be combined with a binder and formed into a monolith. The monolith is placed in thermal contact with the heat-shrinkable film, thereby causing the acid-functional porous sorbent to be in thermal contact with the heat-shrinkable film. The composite construction can be placed in a pouch, for example, that includes holes for passage of the ethylene oxide. Alternatively, it can be placed in a container (e.g., physical pack) that defines a tortuous channel for passage of the ethylene oxide.

Binders for the monolith include organic materials, inorganic materials, or combinations thereof. In certain embodiments, the binder includes an organic polymeric material. In certain embodiments, the organic polymeric material includes a polyelectrolyte material. In certain embodiments, the polyelectrolyte material is derived from natural polymers or modified natural polymers.

In certain embodiments, the polyelectrolyte material is selected from polyamines, polyamides, polyalcohols, polysaccharides, polyacrylamides, polyacrylates, humic acids, proteins, polydiallyldimethylammonium chloride, polydiallyldimethylammonium salts, polyamine-polydiallyldimethylammonium chloride blends, polyquartenary amines, inorganic-polyamine blends, and inorganic polydiallyldimethylammonium chloride blends, cationic starches, cationic polymethylmethacrylates, copolymers of vinylimidazolium methochloride and vinylpyrrolidone, quarternized vinylpyrrolidone/dimethylaminoethyl methacrylate copolymers, polyethyleneimines, and combinations thereof. In certain embodiments, the polyelectrolyte material includes cationic starches.

In certain embodiments, the binder includes metal hydroxides, metal oxides, or combinations thereof. In certain embodiments, the binder includes a metal oxide or hydroxide derived from aluminum, calcium, magnesium, or iron (including polyaluminum sulfates and polyaluminum chlorides). In certain embodiments, the binder includes a material selected from polyorganozirconates, polyorganoaluminates, polysiloxanes, polysilanes, polysilazanes, polycarbosilanes, polyborosilanes, zirconium dimethacrylate, zirconium tetramethacrylate, zirconium 2-ethyl hexanoate, magnesium stearate, aluminum butoxides, aluminum diisopropoxide ethylacetoacetate, tetramethyldisiloxanes, tristrimethylsilylphosphate, tristrimethylsiloxyboron, and combinations thereof.

In certain embodiments, the binder includes a silicate (e.g., a metal silicate). In certain embodiments, the metal silicate includes a sodium silicate (e.g., sodium metasilicate), potassium silicate, calcium silicate, magnesium silicate, and combinations thereof. In certain embodiments, the silicate is sodium metasilicate.

In certain embodiments, the binder includes a thermoplastic polymer. In certain embodiments, the thermoplastic polymer is selected from polyamides (such as nylons), polyolefins (such as polyethylenes, e.g., LDPE, LLDPE, HDPE, polyethylene copolymers with other polyolefins, polypropylenes), polyvinyl chlorides (both plasticized and unplasticized), fluorocarbon resins (such as polytetrafluoroethylene), polystyrenes, cellulosic resins (such as cellulose acetate butyrates), acrylic resins (such as polyacrylates and polymethacrylates), styrene copolymers (such as acrylonitrile-butadiene-styrenes or acrylonitrile-styrenes), polycarbonates, polyvinylacetates, ethylene-vinyl acetates, polyvinyl alcohols, polyoxymethylene, polyformaldehyde, polyacetals, polyesters (such as polyethylene terephthalate), polyether ether ketones, and phenol-formaldehyde resins (such as resols and novolacs), and combinations thereof.

In certain embodiments, the binder includes a thermoset polymer. In certain embodiments, the thermoset polymer is selected from polyurethanes, silicones, fluorosilicones, phenolic resins, melamine resins, melamine formaldehyde, and urea formaldehyde.

In certain embodiments, the binder includes an elastomer. In certain embodiments, the elastomer is selected from natural rubbers, synthetic rubbers (such as styrene-butadiene rubber, polychloroprene (neoprene), nitrile rubber, butyl rubber), silicones, polyurethanes, alkylated chlorosulfonated polyethylenes, polyolefins, chlorosulfonated polyethylenes, perfluoroelastomers, ethylene-propylene-diene terpolymers, chlorinated polyethylene, fluoroelastomers, and combinations thereof.

In certain embodiments, the binder includes a naturally occurring polymer certain embodiments, the naturally occurring polymer is selected from celluloses, collagens, organic acids, and combinations thereof. In certain embodiments, the naturally occurring polymer is a biodegradable polymer. In certain embodiments, the biodegradable polymer is selected from polyethyleneglycols, polylactic acids, polyvinylalcohols, copolymers of polylactideglycolide, cellulose, alginic acid, carrageenans isolated from seaweed, polysaccharides, pectins, xanthans, starches, and combinations thereof. In certain embodiments, the biodegradable polymer is selected from polyethyleneglycols, polylactic acids, polyvinylalcohols, copolymers of polylactideglycolide, and combinations thereof.

In certain embodiments, the binder includes an electrically conductive polymer. In certain embodiments, the electrically conductive polymer is selected from doped polyanilines and polythiophenes.

In certain embodiments, the binder includes a gelling material, an absorbent material, or combinations thereof. In certain embodiments, the absorbent binder material is a superabsorbent material. In certain embodiments, the superabsorbent material is selected from polyacrylic acids, polyacrylamides, polyalcohols, polyamines, polyethylene oxides, cellulose, chitins, gelatins, starches, polyvinyl alcohols, polyacrylic acid, polyacrylonitrile, carboxymethyl cellulose, alginic acid, carrageenans isolated from seaweeds, polysaccharides, pectins, xanthans, polydiallyldimethylammonium chloride, polyvinylpyridine, polyvinylbenzyltrimethylammonium salts, polyvinylacetates, polylactic acids, and combinations thereof.

Exemplary binders also include waxes such as long chain hydrocarbons (e.g., paraffin), long chain aliphatic esters (e.g., carnauba wax), a combination of esters of fatty acids and long chain alcohols (e.g., bees wax), and synthetic waxes (e.g., combinations of the above).

Suitable binders are disclosed, for example, in International Publication No. WO 2018/089870 (3M Innovative Properties Company).

In certain embodiments, a plurality of EO sensors of the present disclosure may be included in an array. In such an array, each of the EO sensors may respond differently to ethylene oxide. The sensors in the array may vary with respect to the sorbent loading, the identity of the acid, concentration of acid in the sorbent, type of heat-shrinkable film, and/or the thickness of the adhesive. Using this variability between sensors of an array can be used, for example, to indicate different levels of ethylene oxide.

The present disclosure also provides a method of detecting ethylene oxide in a sterilization process, the method comprising: providing an ethylene oxide sterilization sensor comprising: a heat-shrinkable film; an acid-functional porous sorbent in thermal contact with the heat-shrinkable film; and an acid having a boiling point above 120° C. and a pKa of no greater than 2.5, wherein the acid is impregnated in or covalently attached to the porous sorbent; allowing ethylene oxide to contact the acid in contact with the porous sorbent to generate thermal energy sufficient to shrink the heat-shrinkable film; and detecting completion of the ethylene oxide sterilization process.

The heat generated from the interaction, which can be both catalytic and reactive, causes a dimensional change (i.e., shrinkage) in the heat-shrinkable film. The shrinkage of the heat-shrinkable film is what indicates proper sterilization. The degree of shrinkage in the film will depend on the amount of heat to which it is exposed, which is, in part, a function of how much EO it "sees."

Typically, sufficient thermal energy is generated at a concentration and/or exposure time that is above the required ethylene oxide concentration (600 mg/L+/−30 mg/L) or exposure time (3 hours at 37° C. or 1 hour at 55° C.) required for the sterilization process. Other parameters of EO sterilization processes include relative humidity (40-60% RH+/−10%) at typical temperatures 37° C. and 55° C. and ambient pressure.

In certain embodiments, the method involves detecting completion by exposing an underlying visual indicator (e.g., image). Alternatively, the method involves detecting completion by creating a visual indicator on the film. Other mechanisms by which completion of an EO sterilization process can be detected would be envisioned by one of skill in the art.

In certain embodiments, shrinkage of the film results in separating or tearing perforations in the heat-shrinkable film.

In certain embodiments, shrinkage in one dimension of a heat-shrinkable film is at least 5%, at least 8%, or at least 10%. In certain embodiments, shrinkage in the total area of a heat-shrinkable film is at least 10%, at least 15%, or at least 18%.

Acid-Functional Porous Sorbent

The porous sorbent that is in thermal contact with the heat-shrinkable film is also in contact with an acid. In this context, an "acid" includes acid compounds as well as acid moieties. The porous sorbent functions as a scaffold for one or more acids, whether such acid is impregnated therein or covalently attached thereto. Hence, such sorbent is referred to herein as an "acid-functional porous sorbent" when it includes covalently attached acid moieties or impregnated acid compounds. The acid-functional porous sorbent is derived from a porous (e.g., microporous, mesoporous, or macroporous) sorbent material.

Suitable acids include acid compounds or acid moieties having a boiling point above 120° C. and a pKa of no greater than 2.5. Examples of acid compounds that may be incorporated into the porous sorbent include sulfuric acid, phosphoric acid, alkyl sulfonic acid, alkyl phosphonic acid, benzene sulfonic acid, and toluene sulfonic acid. In this context, "alkyl" refers to C1-C4 alkyl groups, with methyl and ethyl being preferred. Examples of acid moieties (i.e., acid groups) that may be covalently attached to the porous sorbent include sulfonic acid (—$SO_3H$) and phosphonic acid (—$PO_3H_2$) groups. Various combinations of acid compounds and acid moieties may be used as desired.

In certain embodiments, the acid-functional porous sorbent is present in an amount of at least 10 grams per square meter (gsm), at least 20 gsm, or at least 40 gsm, of heat-shrinkable film. In certain embodiments, the acid-functional porous sorbent is present in an amount of up to 1000 gsm, up to 600 gsm, up to 400 gsm, or up to 250 gsm, of heat-shrinkable film.

In certain embodiments, if the acid is in the form of acid moieties (i.e., acid groups) that are covalently attached to the porous sorbent to form the acid-functional porous sorbent, they are present in an amount of at least 0.2 millimole acid moieties per gram of acid-functional porous sorbent (mmole/g), at least 0.5 mmole/g, at least 1 mmole/g, or at least 2 mmole/g (millimoles of acid moieties per gram of acid-functional porous sorbent). In certain embodiments, if the acid groups are covalently attached to the porous sorbent to form the acid-functional porous sorbent, they are present in an amount of up to 5.5 mmole of acid moieties per gram of acid-functional porous sorbent.

In certain embodiments, if the acid is an acid compound impregnated in the porous sorbent to form the acid-functional porous sorbent, it is present in an amount of at least 5 percent by weight (wt-%), at least 10 wt-%, or at least 20 wt-% based on the total weight of the acid-functional porous sorbent. In certain embodiments, if the acid is an acid compound impregnated in the porous sorbent to form the acid-functional porous sorbent, it is present in an amount of up to 80 wt-%, up to 70 wt-%, or up to 60 wt-%, based on the total weight of the acid-functional porous sorbent.

The "porous" sorbent includes minute spaces or holes through which liquid or air may pass. It may include a microporous, mesoporous, or macroporous material. A mesoporous material is a material having pores with diameters of 2 nanometers to 50 nm, a microporous material is a material having pores smaller than 2 nm in diameter, and a macroporous material is a material having pores larger than 50 nm in diameter.

The amount of nitrogen gas absorbed by the porous sorbent under cryogenic conditions at a relative pressure of 0.98 may be used to measure the total pore volume for pores having diameters up to 50 nanometers. This method measures both micropores and mesopores. The pore volume of the porous sorbent at a relative pressure of 0.98 is often at least 0.4 $cm^3$/gram, at least 0.5 $cm^3$/gram, at least 0.6 $cm^3$/gram, at least 0.8 $cm^3$/gram, at least 1.0 $cm^3$/gram, or at least 1.2 $cm^3$/gram. In some embodiments, the pore volume of the porous sorbent is substantially macroporous and has quite low microporosity and mesoporosity.

Porous sorbents include those that can withstand the acids described herein without degradation. They may include inorganic materials, organic materials, or combinations thereof. Examples include activated carbon, porous silica, zeolites, and porous organic polymers. Combinations of porous sorbents may be used if desired.

In certain embodiments, the porous sorbents include porous organic polymers. In certain embodiments, the porous organic polymers are derived from at least 60 wt-% aromatic monomers. Exemplary porous organic polymers include styrene-divinylbenzene, divinylbenzene-maleic anhydride (such as those described in International Publication No. WO 2017/106434 (3M Innovative Properties Co.)), and other aromatic-containing polymers. Combinations of porous sorbents may be used if desired.

In certain embodiments, the porous organic polymers may be functionalized with sulfonic acid groups or other acid moieties as described herein. A precursor polymeric material (one type of porous sorbent material) that is reacted with an agent that provides such groups (e.g., an acid functionalizing agent such as a sulfonic acid agent) to form the acid-functional porous sorbent is typically formed from a polymerizable composition that contains aromatic monomers. Examples of aromatic monomers include, but are not limited to, styrene, styrene substituted with an alkyl group, divinylbenzene (DVB), and the like. Other examples of aromatic monomers include styrene substituted with a chloromethyl group (e.g., vinylbenzyl chloride). Other examples of aromatic monomers include bis(chloromethyl)-substituted aromatic monomers (e.g., p-xylylene-dichloride or isomers thereof). In some embodiments, at least 60 wt-%, at least 70 wt-%, at least 80 wt-%, at least 85 wt-%, at least 90 wt-%, or at least 95 wt-%, and up to 100 wt-%, up to 99 wt-%, up to 98 wt-%, up to 95 wt-%, or up to 90 wt-% of the monomers in the polymerizable composition are aromatic monomers.

The precursor polymeric material is typically crosslinked, thereby forming one type of porous sorbent. Crosslinking tends to enhance the porosity of the precursor polymeric materials and the resulting acid-functional porous sorbent. Any crosslinking method can be used. For example, in some embodiments, the polymerizable composition contains relatively large amounts of DVB (e.g., at least 10 wt-%) and no post-polymerization crosslinking is used. In other embodiments, the precursor is crosslinked lightly by the addition of relatively low amounts of DVB (e.g., 1 wt-% to less than 10 wt-%) in the polymerizable composition. Further crosslinking occurs post-polymerization using Friedel-Crafts chemistry in the presence of compounds having chloromethyl groups or chloromethylether groups such as, for example, xylylene-dichloride (XDC), 1,4-bi schloromethyldiphenyl (CMDP), monochlorodimethylether (MCDE), tris-(chloromethyl)-mesitylene (CMM), and p,p'-bis-chloromethyl-1,4-diphenylbutane (DPB).

In still other embodiments, the precursor polymeric material can be crosslinked using predominately Friedel-Crafts chemistry by reacting with a linear polymer such as polystyrene. The crosslinking of linear polymers such as polystyrene using Friedel-Crafts chemistry is described, for example, in the reference V. A. Davankov et al., *Reactive Polymers*, 13, 27-42 (1990). A small molecule crosslinker having chloromethyl or chloromethyl ether groups is added. This reference also describes the post-crosslinking of gel-type polymers (e.g., lightly crosslinked polymers such as polystyrene crosslinked with low amounts of DVB such as 1 wt-%) using Friedel-Crafts chemistry.

Alternatively, gel-type polymers can be prepared from a monomer mixture of styrene and vinylbenzyl chloride (VBC) that is crosslinked with low amounts of DVB such as 2 wt-% or less. The gel-type polymers can be crosslinked using Friedel-Crafts chemistry but no small molecule crosslinker having chloromethyl or chloromethyl ether groups is required. Rather, the chloromethyl group of VBC serves as the crosslinking point. That is, the crosslinker is already part of the gel-type polymer. This method is further described in the reference Jou-Hyeon Ahn et al., *Macromolecules*, 627-632 (2006).

Macroporous precursor polymeric materials can be prepared from a mixture of styrene and DVB by suspension, emulsion, or precipitation polymerization methods. In precipitation polymerization processes, styrene and DVB monomer mixtures are polymerized in the presence of various solvents that serve as porogens. This can also be accomplished using an emulsion or suspension polymerization method where the organic phase consists of the monomers and the porogen. With precipitation polymerization processes, the reaction product is a monolith that matches the size and shape of the container used for the polymerization reaction. With the emulsion or suspension processes, however, the final polymeric material is typically in the form of beads (particles). The porosity of the resulting polymeric material can be controlled by selection of the amount and identity of the porogen used, the solids content of the polymerization mixture (organic phase), and the amount of crosslinker (e.g., DVB) that is used.

These polymerization methods are further discussed in references such as the following: M. M. Mohamed et al., *Nanomaterials*, 2, 163-186 (2012); Y. Zhang et al., *Nano Today*, 4, 135-142 (2009); S. Wei et al., *Colloids and Surfaces A: Physiochem. Eng. Aspects*, 414, 327-332 (2012); A. K. Nyhus et al., *J. Poly. Sci. Part A: Polymer Chemistry*, 37, 3973-3990 (1999); Q. Liu et al., *J. Phys. Chem. C*, 112, 13171-13174 (2008); U.S. Pat. No. 3,531,463 (Gustafson et al.), and U.S. Pat. No. 6,416,487 B1 (Braverman et al.).

Other macroporous precursor polymeric materials can be formed using suspension or emulsion polymerization methods like those described above but with lower levels of the DVB crosslinker (e.g., 2 wt-% to 20 wt-%). A portion of the styrene monomers is replaced with VBC. The resulting polymers can be further crosslinked using Friedel-Crafts chemistry. This method is further described in the reference Jou-Hyeon Ahn et al, *Macromolecules*, 627-632 (2006).

Still other precursor polymeric materials can be prepared as discussed in the reference C. D. Wood et al., *Chem. Mater.*, 19, 2034-2048 (2007). In this instance, bis(chloromethyl) aromatic monomers such as p-xylylene-dichloride (XDC) or isomers thereof, 4,4'-bis(chloromethyl)-1,1'-biphenyl, and bis(chloromethyl) anthracene are reacted alone or in combination using Friedel-Crafts chemistry to produce micro-, meso-, and macro-porous precursor polymeric materials for use as porous sorbents.

Alternatively, precursor polymeric materials can be prepared using even simpler aromatic compounds such as benzene and crosslinking the benzene using Friedel-Crafts chemistry and a small molecule crosslinker such as formaldehyde dimethyl acetal as described in B. Li et al., *Macromolecules*, 44, 2410-2414 (2011).

In some embodiments, the precursor polymeric material is formed from a polymerizable composition that contains 10 wt-% to 80 wt-% DVB and 20 wt-% to 90 wt-% styrene-type monomers (i.e., styrene and/or styrene substituted with an alkyl group) based on the total weight of monomers in the polymerizable composition. In many such embodiments, at least 90 wt-%, at least 92 wt-%, at least 95 wt-%, at least 96 wt-%, at least 98 wt-%, at least 99 wt-%, and up to 100 wt-% of the monomers in the polymerizable composition are selected from DVB or a styrene-type monomer.

In some embodiments, the amount of DVB is at least 10 wt-%, at least 20 wt-%, at least 30 wt-%, at least 40 wt-%, at least 50 wt-%, at least 60 wt-%, and up to 80 wt-%, up to 70 wt-%, up to 60 wt-%, up to 50 wt-%, or up to 40 wt-%, based on the total weight of monomers in the polymerizable composition. The remainder of the monomers is often a styrene-type monomer.

The precursor polymeric material (and other porous sorbents) is typically porous and often has a BET specific surface area that is in a range of 25 square meters per gram ($m^2/g$) to 1300 $m^2/g$. The BET specific surface area is often at least 25 $m^2/g$, at least 50 $m^2/g$, at least 100 $m^2/g$, at least 200 $m^2/g$, at least 300 $m^2/g$, at least 400 $m^2/g$, or at least 500 $m^2/g$, and up to 1300 $m^2/g$, up to 1200 $m^2/g$, up to 1100 $m^2/g$, up to 1000 $m^2/g$, 5 up to 900 $m^2/g$, up to 800 $m^2/g$, up to 700 $m^2/g$, up to 600 $m^2/g$, or up to 500 $m^2/g$. In some embodiments, BET specific surface area is in a range of 100 $m^2/g$ to 1000 $m^2/g$, or in a range of 200 $m^2/g$ to 1000 $m^2/g$. Such surface areas also apply to the acid-functional porous sorbents.

In certain embodiments, the precursor polymeric material is treated with an acid-functionalizing agent (e.g., sulfonic acid agent) to form an acid-functional polymeric material (a type of acid-functional porous sorbent). The acid group (e.g., sulfonic acid group ($—SO_3H$)) typically replaces a hydrogen atom that is bonded to a carbon atom that is part of an aromatic ring of the precursor polymer. Any known method can be used to introduce the acid group into the precursor polymeric material.

In some embodiments, the precursor polymeric material is reacted with a halogenated acid, such as a halogenated sulfonic acid (e.g., chlorosulfonic acid) acid-functionalizing agent. The precursor polymeric material is mixed with a solution of the halogenated acid dissolved in an appropriate organic solvent. Suitable organic solvents include various halogenated solvents such as 1,2-dichloroethane, methylene chloride, and chloroform. The precursor polymeric material is often added to the solution of the halogenated acid at a temperature below room temperature. The initial reaction can be quite exothermic so, if adequate care is not taken, the solvent can boil during the addition. After the reactants are combined, the temperature is often increased to any desired temperature such as room temperature up to the temperature associated with reflux conditions. The reaction time can range from a few minutes to 24 hours. After this reaction, the resulting intermediate polymeric material has attached halogenated acid-functional groups (e.g., —$SO_2X$ groups where X is halo such as chloro). The reaction time and the reaction temperature can be varied to prepare polymeric materials with different amounts of the acid (sulfonyl-containing) group.

To prepare the acid moiety (i.e., acid group), such as sulfonic acid group (—$SO_3H$), the intermediate polymeric material with attached halogenated acid-functional group (e.g., —$SO_2X$ group) is placed in water. The conversion of the halogenated groups to the acid groups often can occur at room temperature within 30 minutes, within 1 hour, within 2 hours, within 4 hours, within 8 hours, within 12 hours, within 24 hours, within 36 hours, within 48 hours, within 60 hours, or within 72 hours.

In other embodiments, the precursor polymeric material is reacted with concentrated sulfuric acid or with concentrated sulfuric acid in the presence of a catalyst such as silver sulfate. When a catalyst is present, the reaction typically proceeds faster.

With or without the catalyst, the reaction temperature is often in a range of room temperature (e.g., 20-25° C.) to 150° C., in a range of room temperature to 125° C., or in a range of room temperature to 100° C. The reaction times can vary from a few minutes (e.g., 5 minutes, 10 minutes, or 30 minutes) to 24 hours or longer. As with halogenated sulfonic acid, the reaction time and the reaction temperature can be varied to prepare polymeric materials with different amounts of the sulfonic acid group. After this reaction, the resulting polymeric material has attached acid groups (e.g., —$SO_3H$ groups), thereby forming an acid-functional porous sorbent.

Heat-Shrinkable Film

Useful heat-shrinkable films (i.e., polymer sheets) are also known as shape-memory films (i.e., polymer sheets). Useful heat-shrinkable films may include physically and/or chemically crosslinked polymers.

Suitable physically crosslinked films include linear block copolymers such as thermoplastic polyurethane elastomers with hard segments and soft switching segments. Multi-block copolymers can also serve as films such as, for example, polyurethanes with polystyrene and poly(1,4-butadiene) blocks; ABA tri-block copolymers of poly(tetrahydrofuran) and poly(2-methyl-2-oxazoline); polyhedral oligomeric silsesquioxane (POSS)-modified polynorbomene; and polyethylene/Nylon-6 graft copolymers.

Suitable chemically crosslinked films include, but are not limited to, crosslinked high density polyethylene, crosslinked low-density polyethylene, and crosslinked copolymers of ethylene and vinyl acetate.

Other examples of heat-shrinkable films include polymers selected from polyurethanes, polynorbornenes, polyethers, polyacrylates, polyamides, polysiloxanes, polyether amides, polyether esters, trans-polyisoprenes, polymethyl methacrylates, crosslinked trans-polyoctylenes, crosslinked polyethylenes, crosslinked polycyclooctenes, inorganic-organic hybrid polymers, copolymer blends with polyethylene and styrene-butadiene co-polymers, urethane-butadiene copolymers, polymethyl methacrylate, polycaprolactone, and oligocaprolactone copolymers.

Suitable heat-shrinkable films include polymers such as those described in U.S. Pat. No. 5,506,300 (Ward et al); U.S. Pat. No. 5,145,935 (Hayashi); U.S. Pat. No. 5,665,822 (Bitler et al); U.S. Pat. No. 6,160,084 (Langer); U.S. Pat. No. 6,388,043 (Langer); U.S. Pat. No. 5,155,199 (Hayashi); U.S. Pat. No. 7,173,096 (Mather et al.); U.S. Pat. No. 4,436,858 (Klosiewicz); U.S. Pat. No. 6,423,421 (Banaszak); and U.S. Pat. Appl. Publ. Nos. 2005/244353 (Lendlein et al), U.S. 2007/009465 (Lendlein et al), and 2006/041089 (Mather et al).

Heat-shrinkable polymer films (sheets or rolls) can be processed by heating them to near or above the heat-shrinkable (i.e., shape-memory) transition temperature range of the particular material utilized, then orienting the sheet by stretching or tentoring it in at least one direction (typically down-web when a roll-to-roll process is used) followed by cooling the sheet to lock in the strain caused by the stretching. In some embodiments, the sheet can be oriented in two or more directions. For example, biaxially oriented films can be made by simultaneous down-web and cross-web stretching of the polymer film near or above its transition temperature range followed by cooling. Biaxially oriented films or sheets can have a maximum shrink tension in one direction.

The heat-shrinkable films of the sterilization sensors of the present disclosure reach a temperature at or above that which the shrink tension of the heat-shrinkable polymer is sufficiently high to cause a substantial change in one or more dimensions of the sheet. The process of making and orienting heat-shrinkable polymer sheets is well known to those having ordinary skill in the art.

In certain embodiments, the sterilization sensors of the present disclosure include a heat-shrinkable film with an area having a strained temporary shape, and includes at least one of a plurality of perforations having a width therein and a total length. When heated to or above a transition temperature range, the heat-shrinkable polymer sheet at least partially converts from its strained temporary shape to its intrinsic shape. The intrinsic shape of the heat-shrinkable film is the shape to which it returns after the polymer is heated to or above a transition temperature range.

In certain embodiments, it is possible to anneal some heat-shrinkable polymers by heating them to a temperature close to but below the transition temperature range. Depending upon the composition of the polymer, such annealing can cause the temporary shape of the heat-shrinkable polymer to change and substantially eliminate the potential for small changes in shape at temperatures below the shape memory transition temperature range.

Examples of commercially available thermoplastic films include: polyurethanes available under the trade designation DIARY, including the MM, MP, MS, and MB (microbead powder) types series available from SMP Technologies, Inc. of Tokyo, Japan; elastic memory composites available under the trade designation EMC from Composite Technology Development, Inc. of Lafayette, CO; and polymers available under the trade designation VERIFLEX from Cornerstone Research Group, Inc. of Dayton, OH. The shape memory properties of acrylonitrile-butadiene-styrene (ABS) copolymers, polycarbonate, and polyethylene terephthalate are also disclosed by Hussein et al., in "New Technologies for Active Disassembly: Using the Shape Memory Effect in Engineering Polymers, *J. Product Development*, 6, 431-449 (2008).

Additional examples of commercially available heat-shrinkable films that can be converted into various shapes include those heat-shrinkable films available under the trade designations CORTUFF, CRYOVAC, and OPTI from Sealed Air Inc. of Elmwood Park, NJ. Additional examples include heat-shrinkable films available under the trade designations SHRINKBOX, VHG, EZ, AFG, ABL and PLAnet from Bemis Clysar of Oshkosh, WI.

Optional Adhesive

In certain embodiments, the acid-functional porous sorbent is adhered to the heat-shrinkable film using a layer of an adhesive. The layer of adhesive may be continuous or discontinuous. It may be laminated to the film or coated thereon (e.g., pattern coated). It may be a double-sided transfer adhesive, a sprayable adhesive, or a hot-melt adhesive.

Exemplary adhesives include those described, for example, in U.S. Pat. No. 7,893,179 (Anderson et al.) and U.S. Pat. No. 9,134,251 (Thomas et al.). For example, the adhesive may include a natural rubber adhesive, a synthetic rubber adhesive, a poly-alpha-olefin adhesive, a styrene block copolymer adhesive, a poly(meth)acrylate adhesive, a silicone adhesive, or mixtures thereof.

The layer of adhesive can function as a buffer or insulator. Thus, the thickness of the adhesive can be tailored to control the level of shrinkage. A typical adhesive layer thickness is at least 1 micron, or at least 25 microns, and often up to 2500 microns, or up to 200 microns.

Exemplary EO Sterilization Sensors

The EO sterilization sensors can be incorporated into formats of known sterilization sensors as long as they include: a heat-shrinkable film; an acid-functional porous sorbent in thermal contact (which does not necessarily mean direct contact) with the heat-shrinkable film; and an acid having a boiling point above 120° C. and a pKa of no greater than 2.5, wherein the acid is impregnated in or covalently attached to the porous sorbent.

For example, U.S. Pat. No. 4,138,216 (Larsson et al.) discloses an EO sterilization sensor, and U.S. Pat. No. 4,448,548 (Foley) and U.S. Pat. No. 5,378,430 (Nieves et al.) disclose steam sterilization sensors, which can be adapted to include the acid-functional porous sorbent and heat-shrinkable film as disclosed herein. Other known sterilization sensors can be adapted by one of skill in the art to include the acid-functional porous sorbent and heat-shrinkable film as disclosed herein. These include, for example, U.S. Pat. No. 5,451,372 (Larsson et al.), U.S. Des 315,600 (Niven), and RE 34,515 (Foley). Sensors of the present disclosure can be in a variety of shapes and sizes. Typical sensors include a smallest dimension of at least 2.5 centimeters, to avoid getting lost in a sterilizer.

The heat-shrinkable film can be attached at one end to a backing sub state (e.g., a thin aluminum film, molded plastic sheet, paper, foil, etc.). The acid-functional porous sorbent is in thermal contact with the film (e.g., adhered thereto), and between the backing and the heat-shrinkable film; a visual indicator (e.g., picture, word, or colored feature) is disposed.

FIGS. 1-7 are representative EO sterilization sensors.

Figure 1A:
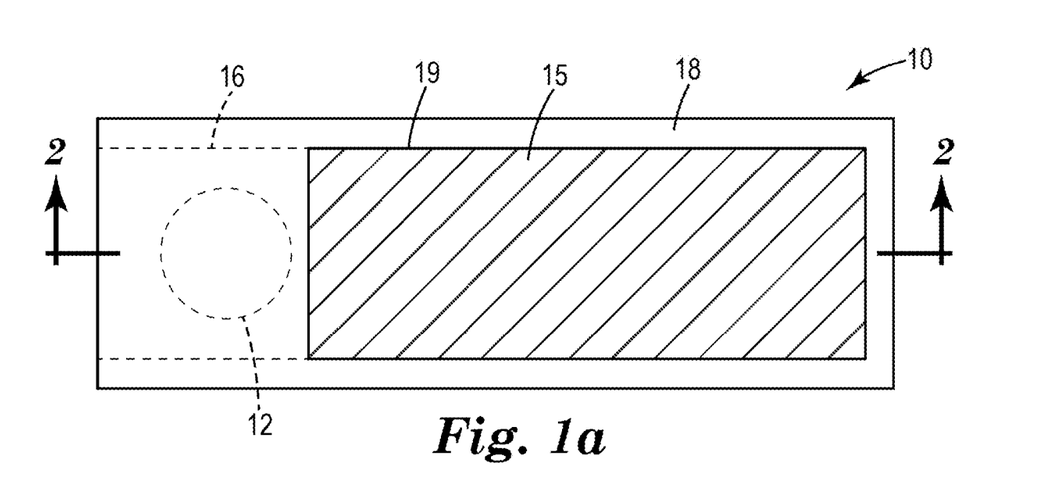
FIG. 1a represents the sterilization sensor before activation by ethylene oxide and FIG. 1b represents the sterilization sensor after activation by ethylene oxide.
Figure 1B:
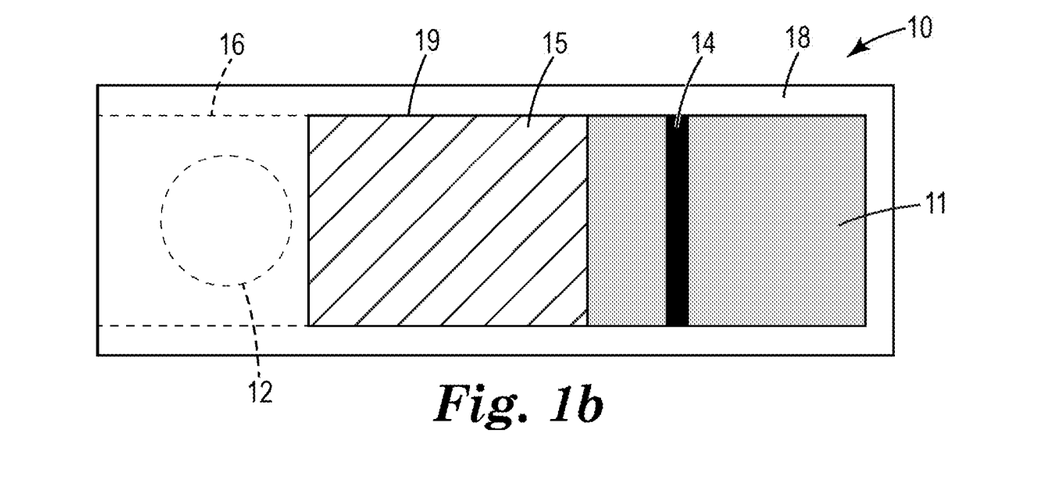
Figure 2:
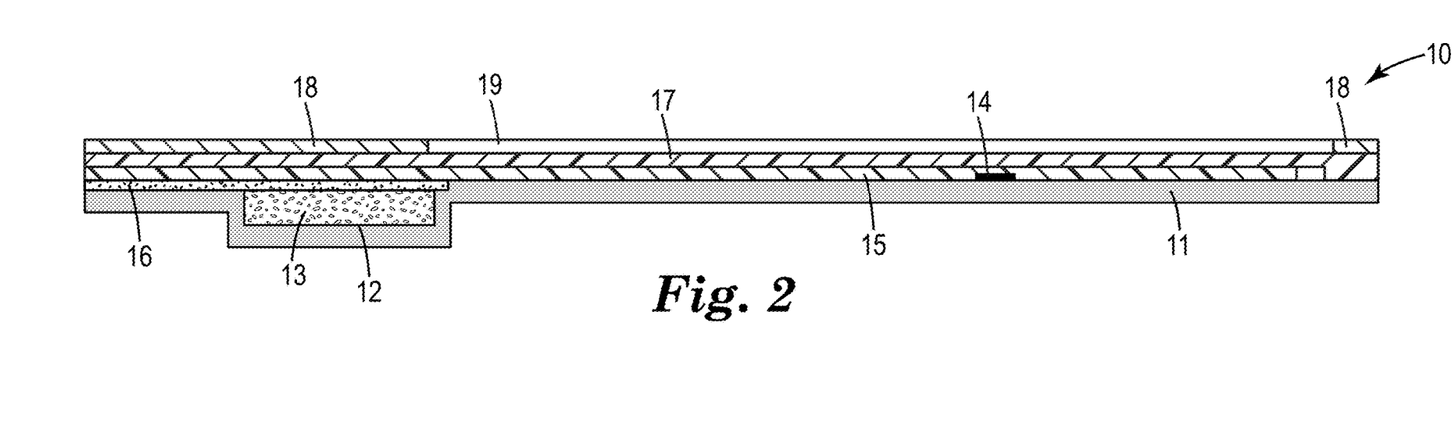

FIG. 1 is a top view of one embodiment of an EO sterilization sensor of the present disclosure, wherein FIG. 1a represents the sterilization sensor before activation by ethylene oxide and FIG. 1b represents the sterilization sensor after activation by ethylene oxide. FIG. 2 is a cross-section of the EO sterilization sensor of FIG. 1.

Referring to FIGS. 1a, 1b, and 2, the EO sterilization sensor 10 includes a backing substrate 11 (not shown in FIG. 1a) that includes a reservoir 12 (represented by a dashed line in the form of a circle in FIGS. 1a and 1b) for holding the acid-functional porous sorbent 13 (not shown in FIG. 1a or 1b). Disposed on the backing substrate 11 is visual indicator 14 (e.g., an image such as a picture or word, or a colored feature); such as the black line shown in FIG. 1b. Disposed on the backing substrate 11 (and the visual indicator 14) is a heat-shrinkable film 15, which is adhered to the backing substrate 11 at one end using an adhesive 16 (region of adhesive is represented by a dashed line in the form of a rectangle in FIGS. 1a and 1b). The adhesive 16 locks the heat-shrinkable film 15 in place at one end of the sensor, which causes any shrinkage to move toward the immobilized end in a generally linear fashion. The adhesive 16 also provides thermal contact between the acid-functional porous sorbent 13 and the heat-shrinkable film 15. The EO sterilization sensor 10 may also include a transparent film 17 (e.g., thermoplastic film not shown in FIGS. 1a and b) disposed on the heat-shrinkable film 15, although this is optional. The topmost layer is a cover film 18 (e.g., paper, thermoplastic film) that includes a window 19, through which the heat-shrinkable film 15 is visible. This window 19 may simply be a cut-out creating an opening in the cover film 18.

FIG. 1a shows the heat-shrinkable film 15 prior to EO sterilization, which involves an exothermic interaction between ethylene oxide and the acid in the acid-functional porous sorbent. The heat generated from the interaction causes a dimensional change in the heat-shrinkable film 15. The resultant dimensional change (i.e., shrinkage) of the heat-shrinkable film 15 reveals the visual indicator (e.g., a black line) 14 after proper sterilization, which is demonstrated by FIG. 1b.

Figure 3A:
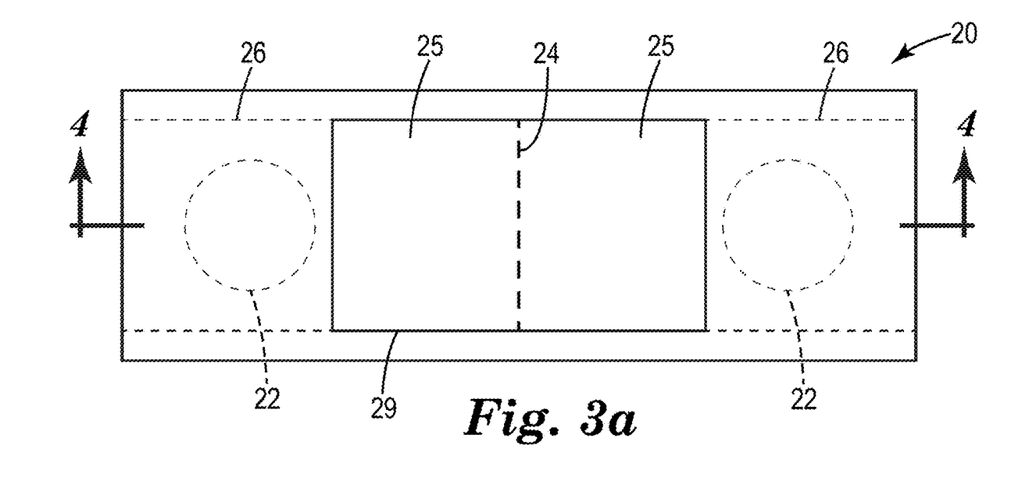
FIG. 3a represents the sterilization sensor before activation by ethylene oxide and FIG. 3b represents the sterilization sensor after activation by ethylene oxide.
Figure 3B:
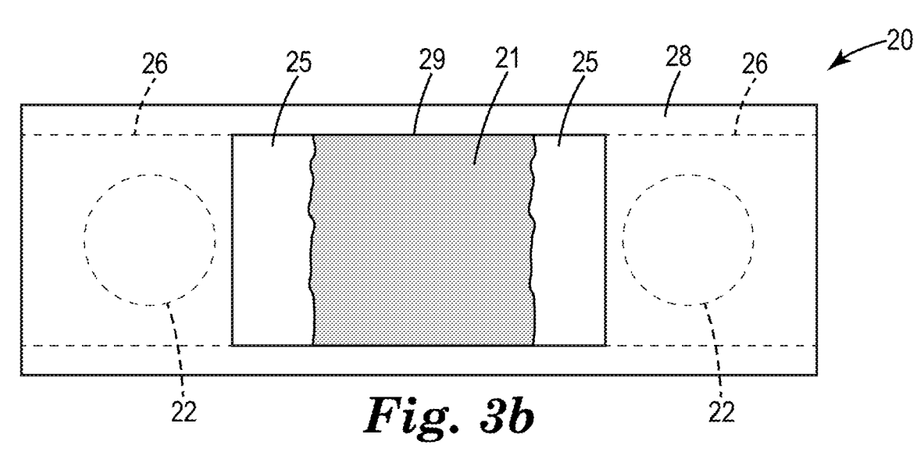
Figure 4:
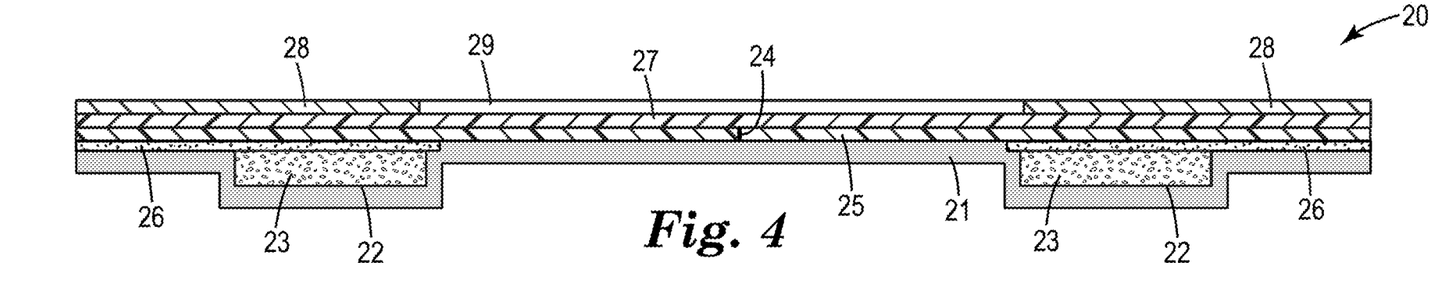

Referring to FIGS. 3a, 3b, and 4, the EO sterilization sensor 20 includes a backing substrate 21 (not shown in FIG. 3a) that includes two reservoirs 22 (each represented by a dashed line in the form of a circle in FIGS. 3a and 3b) for holding the acid-functional porous sorbent 23 (not shown in FIG. 3a or 3b). Disposed on the backing substrate 21 is a heat-shrinkable film 25 that includes a perforated line 24. The heat-shrinkable film 25 is adhered to the backing substrate 21 at both ends using an adhesive 26 (each region of adhesive represented by a dashed line in the form of a rectangle in FIGS. 3a and 3b). The adhesive 26 locks the heat-shrinkable film 25 in place at both ends of the sensor, which causes any shrinkage to move toward the immobilized ends in a generally linear fashion. The adhesive 26 also provides thermal contact between the acid-functional porous sorbent 23 and the heat-shrinkable film 25. The LO sterilization sensor 20 may also include a transparent film 27 (e.g., thermoplastic film not shown in FIGS. 3a and 3h) disposed on the heat-shrinkable film 25, although this is optional. The topmost layer is a cover film 28 (e.g., paper, thermoplastic film) that includes a window 29, through which the heat-shrinkable film 25 is visible. This window 29 may simply be a cut-out creating an opening in the cover film 28.

FIG. 3a shows the heat-shrinkable film 25 prior to EO sterilization, which involves an exothermic interaction between ethylene oxide and the acid in the acid-functional porous sorbent. The heat generated from the interaction causes a dimensional change in the heat-shrinkable film 25. The resultant dimensional change (i.e., shrinkage) of the heat-shrinkable film 25 causes the perforated line 24 to completely perforate and the heat-shrinkable film 25 to separate into two pieces and reveal the backing substrate 21 (which would typically be in a different color for easy visualization) after proper sterilization. This is demonstrated by FIG. 3b. The degree of shrinkage and separation between the two pieces of the heat-shrinkable film 25 will depend on the amount of heat to which it is exposed, which is, in part, a function of how much ethylene oxide it sees.

Figure 5:
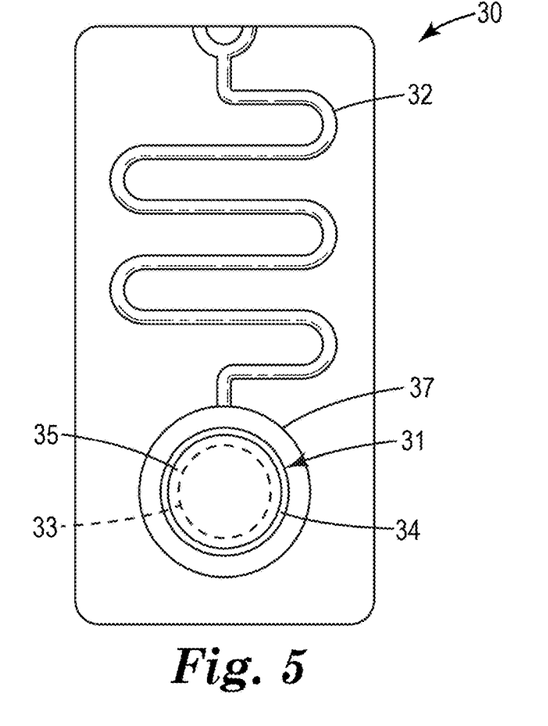
FIG. 5 is a top view of a physical pack holding another embodiment of an EO sterilization sensor of the present disclosure.
Figures 6A, 6B:
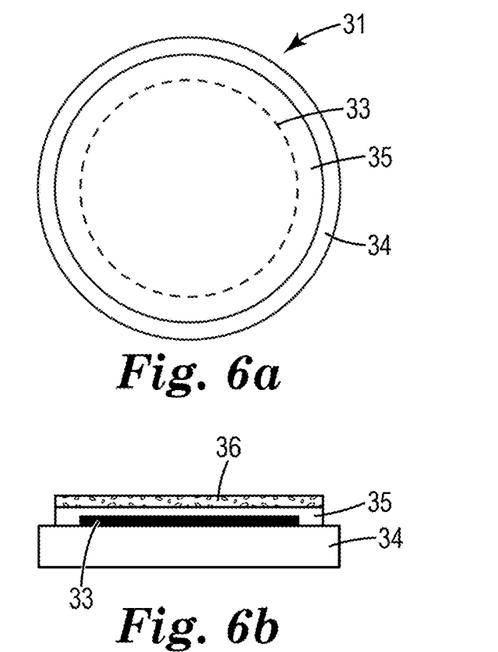
Figure 7A:
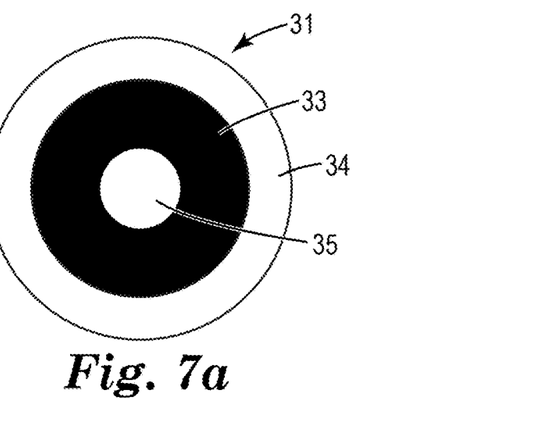
FIG. 7a represents a top view and FIG. 7b a cross-sectional view.
Figure 7B:
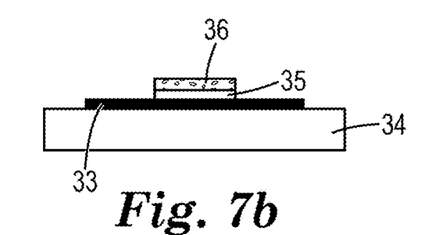

FIG. 5 is a top view of a physical pack holding another embodiment of an EO sterilization sensor of the present disclosure. FIG. 6 is a representation of the EO sterilization sensor of FIG. 5 before activation by ethylene oxide, wherein FIG. 6a represents a top view and FIG. 6b a cross-sectional view. FIG. 7 is a representation of the EO sterilization sensor of FIG. 5 after activation by ethylene oxide, wherein FIG. 7a represents a top view and FIG. 7b a cross-sectional view.

Referring to FIGS. 5, 6a, 6b, 7a, and 7b, the physical pack 30 includes an EO sterilization sensor 31. The physical pack 30 includes a molded backing (e.g., a thermoplastic backing) that includes a tortuous channel 32 and a reservoir 33, in which is placed the EO sterilization sensor 31. A transparent film (e.g., transparent thermoplastic layer) is adhered to the molded backing to allow visualization of the change in the EO sterilization sensor 31 upon proper EO sterilization. The tortuous channel 32 provides a passage through with the ethylene oxide diffuses through the physical pack 31 into the reservoir 33 where it contacts the sterilization sensor 31. The sterilization sensor 31 includes a backing substrate 34 on which is disposed a visual indicator 33 (e.g., an image such as a picture or word, or a colored feature), such as the black circle, which represented by the dashed line in FIGS. 5 and 6a and the black circle in FIG. 7a Covering the visual indicator 33 and disposed on the backing substrate 34 is a heat-shrinkable film 35 that includes acid-functional porous sorbent 36 disposed thereon (or incorporated therein). The heat-shrinkable film 35, which is in the form of a circle, is adhered to the backing substrate 34 at the center of the heat-shrinkable film 35. FIGS. 6a and 6b show the heat-shrinkable film 35 prior to EO sterilization. The heat generated from the interaction causes a dimensional change in the heat-shrinkable film 35, which forms a smaller circle and reveals the visual indicator 33 after proper sterilization. The resultant heat-shrinkable film 35 forms a smaller circle (i.e., a donut hole) as shown FIGS. 7a and 7b. While the sterilization sensor 31 is shown to be circular in this embodiment, any shape could be envisioned.

EXEMPLARY EMBODIMENTS

Embodiment 1 is an ethylene oxide sterilization sensor comprising: a heat-shrinkable film; an acid-functional porous sorbent in thermal contact (which does not necessarily mean direct contact) with the heat-shrinkable film; and an acid having a boiling point above 120° C. and a pKa of no greater than 2.5, wherein the acid is impregnated in or covalently attached to the porous sorbent.

Embodiment 2 is the sterilization sensor of any previous embodiment wherein the acid-functional porous sorbent comprises a microporous, mesoporous, or macroporous material.

Embodiment 3 is the sterilization sensor of embodiment 1 or 2 wherein the porous sorbent of the acid-functional porous sorbent comprises an inorganic material, organic material, or a combination thereof.

Embodiment 4 is the sterilization sensor of embodiment 3 wherein the porous sorbent comprises activated carbon, porous silica, zeolites, porous organic polymers, or combinations thereof.

Embodiment 5 is the sterilization sensor of embodiment 4 wherein the porous sorbent comprises a porous organic polymer.

Embodiment 6 is the sterilization sensor of embodiment 5 wherein the porous organic polymer is derived from at least 60 wt-% aromatic monomers.

Embodiment 7 is the sterilization sensor of embodiment 5 or 6 wherein the porous organic polymer comprises styrene-divinylbenzene or divinylbenzene-maleic anhydride.

Embodiment 8 is the sterilization sensor of any previous embodiment wherein the acid-functional porous sorbent is present in an amount of at least 10 grams per square meter (gsm), at least 20 gsm, or at least 40 gsm, of heat-shrinkable film.

Embodiment 9 is the sterilization sensor of any previous embodiment wherein the acid-functional porous sorbent is present in an amount of up to 1000 gsm, up to 600 gsm, up to 400 gsm, or up to 250 gsm, of heat-shrinkable film.

Embodiment 10 is the sterilization sensor of any previous embodiment wherein the acid comprises acid compounds, acid moieties, or combinations thereof. Embodiment 11 is the sterilization sensor of embodiment 10 wherein the acid is in the form of acid moieties (i.e., acid groups) that are covalently attached to the porous sorbent.

Embodiment 12 is the sterilization sensor of embodiment 11 wherein the acid moieties are present in an amount of at least 0.2 millimole, at least 0.5 mmole, at least 1 mmole, or at least 2 mmole, of acid moieties per gram of acid-functional porous sorbent.

Embodiment 13 is the sterilization sensor of embodiment 11 or 12 wherein the acid moieties are present in an amount of up to 5.5 mmole of acid moieties per gram of acid-functional porous sorbent.

Embodiment 14 is the sterilization sensor of any of embodiments 11 through 13 wherein the acid comprises covalently attached acid moieties selected from sulfonic acid ($-SO_3H$) groups, phosphonic acid ($-PO_3H_2$) groups, and a combination thereof.

Embodiment 15 is the sterilization sensor of any of embodiments 10 through 14 wherein the acid is an acid compound impregnated in the porous sorbent.

Embodiment 16 is the sterilization sensor of embodiment 15 wherein the acid compound is present in an amount of at least 5 percent by weight (wt-%), at least 10 wt-%, or at least 20 wt-%, based on the total weight of the acid-functional porous sorbent.

Embodiment 17 is the sterilization sensor of embodiment 15 or 16 wherein the acid compound is present in an amount of up to 80 wt-%, up to 70 wt-%, or up to 60 wt-%, based on the total weight of the acid-functional porous sorbent.

Embodiment 18 is the sterilization sensor of any of embodiments 15 through 17 wherein the acid compound comprises sulfuric acid, phosphoric acid, alkyl sulfonic acid (e.g., with C1-C4 alkyl groups, such as methanesulfonic acid), alkyl phosphonic acid (e.g., with C1-C4 alkyl groups, such as methanephosphonic acid), benzene sulfonic acid, toluene sulfonic acid, or a combination thereof.

Embodiment 19 is the sterilization sensor of any previous embodiment wherein the heat-shrinkable film comprises a physically and/or chemically crosslinked polymer.

Embodiment 20 is the sterilization sensor of embodiment 19 wherein the heat-shrinkable film comprises a thermoplastic polyurethane elastomer, a polyurethane with polystyrene and poly(1,4-butadiene) blocks, an ABA tri-block copolymer of poly(tetrahydrofuran) and poly(2-methyl-2-oxazoline), a polyhedral oligomeric silsesquioxane-modified polynorbornene, a polyethylene/Nylon-6 graft copolymer, a polyethylene, a copolymer of ethylene and vinyl acetate, a polyurethane, a polynorbornene, a polyether, a polyacrylate, a polyamide, a polysiloxane, a polyether amide, a polyether ester, a trans-polyisoprene, a polymethyl methacrylate, a polyoctylene, a polycyclooctenes, an inorganic-organic hybrid polymer, a copolymer blend of polyethylene and a styrene-butadiene copolymer, a urethane-butadiene copolymer, a polymethyl methacrylate, a polycaprolactone, an oligocaprolactone copolymer, or combinations thereof.

Embodiment 21 is the sterilization sensor of any of the previous embodiments wherein the acid-functional porous sorbent is adhered to the heat-shrinkable film.

Embodiment 22 is the sterilization sensor of embodiment 21 wherein the acid-functional porous sorbent is adhered to the heat-shrinkable film using a layer of adhesive comprising a natural rubber adhesive, a synthetic rubber adhesive, a poly-alpha-olefin adhesive, a styrene block copolymer adhesive, a poly(meth)acrylate adhesive, a silicone adhesive, or mixtures thereof.

Embodiment 23 is the sterilization sensor of embodiment 22 wherein the adhesive layer has a thickness of at least 1 micron, or at least 25 microns.

Embodiment 24 is the sterilization sensor of embodiment 22 or 23 wherein the adhesive layer has a thickness of up to 2500 microns, or up to 200 microns.

Embodiment 25 is the sterilization sensor of any previous embodiment wherein the acid-functional porous sorbent is combined with a binder and formed into a monolith.

Embodiment 26 is the sterilization sensor of embodiment 25 wherein the binder comprises an organic material, inorganic material, or a combination thereof.

Embodiment 27 is an array comprising a plurality of the ethylene oxide sterilization sensors described in embodiments 1 through 26.

Embodiment 28 is the array of embodiment 27 wherein the sensors in the array vary with respect to at least one of sorbent loading, identity of acid, concentration of acid in the sorbent, type of heat-shrinkable film, and the thickness of the adhesive.

Embodiment 29 is a method of detecting ethylene oxide in a sterilization process, the method comprising:
providing an ethylene oxide sterilization sensor comprising:
a heat-shrinkable film;
an acid-functional porous sorbent in thermal contact with the heat-shrinkable film; and
an acid having a boiling point above 120° C. and a pKa of no greater than 2.5, wherein the acid is impregnated in or covalently attached to the porous sorbent;
allowing ethylene oxide to contact the acid in contact with the porous sorbent to generate thermal energy sufficient to shrink the heat-shrinkable film; and
detecting completion of the ethylene oxide sterilization process.

Embodiment 30 is the method of detecting of embodiment 29 wherein detecting completion comprises exposing an underlying image.

Embodiment 31 is the method of detecting of embodiment 29 wherein detecting completion comprises creating an image on the film.

Embodiment 32 is the method of embodiment 29 or 30 wherein detecting completion comprises separating or tearing perforations in the heat-shrinkable film.

Embodiment 33 is the method of any of embodiments 29 through 32 wherein sufficient thermal energy is generated at a concentration and/or exposure time that is above the required ethylene oxide concentration (600 mg/L+/−30 mg/L) or exposure time (3 hours at 37° C. or 1 hour at 55° C.) required for the sterilization process.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims. Unless otherwise stated, all amounts are in weight percent.

TABLE 1

List of Materials and Suppliers.

| Material | Supplier |
|---|---|
| Glass micro slide (2-inch × 3-inch) (51-mm × 76-mm) | Erie Scientific (Ramsey, MN, USA) |
| 5-mil (0.13 mm) 467MP transfer adhesive, 2-inch (51-mm) wide | 3M Company (St. Paul, MN, USA) |
| CLYSAR SHRINKBOX 1525 | Bemis Company (Neenah, WI, USA) |
| 6-mil (0.15 mm) 410M double coated tape | 3M Company (St. Paul, MN, USA) |
| AMBERLYST 15H | Sigma-Aldrich (St. Louis, MO, USA) |
| AMBERLITE XAD-2 | Sigma-Aldrich (St. Louis, MO, USA) |
| Silver Sulfate ($Ag_2SO_4$) | Alfa Aesar (Haverhill, MA, USA) |
| Sulfuric Acid (18.0M) ($H_2SO_4$) | EMD Millipore (Burlington, MA, USA) |
| Methanol (MeOH) | Merck (Dramstadt, Germany) |
| PICATOX AMHS37 | Jacobi Carbons (Kalmar, Sweden) |
| ADDSORB GA1 carbon | Jacobi Carbons (Kalmar, Sweden) |
| Propionic acid | Avantor Performance Materials (Radnor, PA) |
| Sodium hydroxide (0.1N) (NaOH) | EMD Millipore (Burlington, MA, USA) |
| Hydrochloric acid (0.1N) (HCl) | Avantor Performance Materials (Radnor, PA) |

Procedure for Determination of Acid Concentration by Liquid Titration:

The acid-functional porous sorbent (about 0.200 gram) was suspended in 20 mL of 0.1 N aqueous (aq.) sodium hydroxide (NaOH). To this suspension was added 3 drops of a 1 percent by weight (wt-%) aqueous solution of phenolphthalein which caused the suspension to turn a pink color. This suspension was titrated with 0.1 Normal (N) aqueous hydrogen chloride (HCl) until the pink color disappeared and the suspension became clear (phenolphthalein endpoint). The acid concentration was calculated based on the amount of acid needed to reach the titration endpoint, reported as milliequivalents per gram (meq/g).

Ethylene Oxide Sterilization Test

A Steri-Vac Sterilizer GS5X-1D manufactured by 3M Company (St. Paul, MN, USA) was used to expose all ethylene oxide (EO) reactive sensors to sterilization conditions of EO to determine their response. A standard sterilization cycle was used in this experiment, which had exposure conditions of 55° C. at 50% Relative Humidity (RH) for 1 hour. A 4-100 EO cartridge was used to produce a concentration of approximately 735 milligrams per liter (mg/L) of EO during the exposure.

Preparatory Example 1 (PE-1)

In a 2 L round bottom flask equipped with a stir bar, 0.7990 gram (g) (2.56 mmol) of silver sulfate ($Ag_2SO_4$) was dissolved in 600 mL of concentrated (18.0 M) sulfuric acid ($H_2SO_4$). To this solution was added slowly 100.06 g of AMBERLITE XAD-2 (nonionic macroreticular styrene/divinylbenzene (St/DVB) copolymer) as received (the as received material was approximately 60 wt-% water so the actual amount of resin added was approximately 40 g). The round bottom flask was stoppered and placed in a sand bath. The reaction mixture was stirred at 100° C. overnight.

After reacting at 100° C. for 18 hours, the round bottom flask was removed from the sand bath and allowed to cool to room temperature. In a 4-L Erlenmeyer flask, 3.0 L of 6 M aq. $H_2SO_4$ was prepared by adding 1.0 L of 18.0 M $H_2SO_4$ slowly to 2.0 L of deionized water. The contents of the round bottom flask were slowly poured into the stirred 3.0 L of 6 M aqueous $H_2SO_4$. This mixture was then vacuum filtered to isolate the solids. The solids were washed with 2.0 L of ultra-pure water (approximately 18 M Ohm resistivity). The pH of the last 100 mL of the ultra-pure water rinse was neutral. The solids were then washed with 1.0 L of methanol (MeOH), and the MeOH was removed by vacuum filtration. The solids were placed in a batch oven and dried overnight at 120° C. Titration results showed the acid-functional porous sorbent to have acid equivalents of 2.41 meq/g.

Preparatory Example 2 (PE-2)

In a 4-ounce (118-mL) jar, 5.00 g of ADDSORB GA1 carbon (20×50 mesh) was added to an aqueous solution of propionic acid prepared by dissolving 10 mL (134 mmol) of propionic acid in 40 mL of deionized water. The jar was then sealed and placed on a jar roller at room temperature for 16 hours. The solids were isolated by vacuum filtration, transferred to a drying dish and dried in a batch oven at 80° C. for 4 hours. Titration results showed the acid functional sorbent to have acid equivalents of 2.90 meq/g.

Examples 1-13 (EX-1 to EX-13)

Examples 1-13 (EX-1 to EX-13) were EO sensors prepared using the following procedure. A 2-inch (51-mm) wide strip of 467MP transfer adhesive, with the liner still on one side, was laminated onto CLYSAR SHRINKBOX 1525 (polyethylene heat-shrinkable film). A roller was passed over the transfer adhesive several times to ensure complete contact with the heat-shrinkable film. The laminated material was then cut into a 1.5-inch×1.5-inch (38-mL×38-mL) square. In one of the corners of the laminated materials, a 1-$cm^2$ piece of 410M double coated tape (liner still on one side) was laminated to the heat-shrinkable film side. A roller was passed over the materials again to ensure proper lamination. The liner was removed from the 1-$cm^2$ piece of double coated tape, and then the stack was laminated into the center of the 2-inch×3-inch (51-mm×76-m) glass slide with the 467MP lined transfer adhesive being the top layer. A roller was again passed over the sample to ensure proper lamination of all the layers. A permanent marker was then used to outline the original dimensions of the stack and was used as a reference to measure the percentage of shrinkage after EO exposure.

The liner on the 467MP transfer adhesive was then removed to expose the adhesive and allow the acid-functional porous sorbent to be bonded to the stack by pouring the acid-functional porous sorbent over the exposed adhesive. A series of EO sensors were prepared using various acid-functional porous sorbents—including the acid-functional porous sorbent of PE-1, AMBERLYST 15H (macroreticular polystyrene with sulfonic acid groups) and PICATOX AMHS37 (sulfuric acid impregnated activated carbon)—by adhering particles of the acid-functional porous sorbent to each sensor at a specific sorbent loading as detailed in TABLE 2. To ensure good adhesion of the acid-functional porous sorbent, a piece of computer paper was placed over the entire sensor, and a rubber roller was used to lightly press the sorbent particles into the adhesive, taking care to not crush the sorbent particles or break the glass slide.

Each sensor was exposed to EO using the EO Sterilization Test described above. The response of each sensor, measured as a percentage of shrinkage of the heat-shrinkable film, is summarized in TABLE 2.

Comparative Example 1 (CE-1)

A 2-inch (51-mm) wide strip of 467MP transfer adhesive, with the liner still on one side, was laminated onto CLYSAR SHRINKBOX 1525. A roller was passed over the transfer adhesive several times to ensure complete contact with the heat-shrinkable film. The laminated material was then cut into a 1.5-inch×1.5-inch (38-mL×38-mL) square. In one of the corners of the laminated materials, a 1-$cm^2$ piece of 410M double coated tape (liner still on one side) was laminated to the heat-shrinkable film side. A roller was passed over the materials again to ensure proper lamination. The liner was removed from the 1-$cm^2$ piece of double coated tape, and then the stack was laminated into the center of the 2-inch×3-inch (51-mm×76-mm) glass slide with the 467MP lined transfer adhesive being the top layer. A roller was again passed over the sample to ensure proper lamination of all the layers. A permanent marker was then used to outline the original dimensions of the stack and was used as a reference to measure the percentage of shrinkage after EO exposure. The liner on the 467MP transfer adhesive was then removed to expose the adhesive.

The sensor CE-1 was exposed to EO using the EO Sterilization Test described above. The response of the sensor CE-1, measured as a percentage of shrinkage of the heat-shrinkable film, is summarized in TABLE 2.

Comparative Example 2 (CE-2)

A 2-inch (51-mm) wide strip of 467MP transfer adhesive, with the liner still on one side, was laminated onto CLYSAR SHRINKBOX 1525. A roller was passed over the transfer adhesive several times to ensure complete contact with the heat-shrinkable film. The laminated material was then cut into a 1.5-inch×1.5-inch (38-mL×38-mL) square. In one of the corners of the laminated materials, a 1-$cm^2$ piece of 410M double coated tape (liner still on one side) was laminated to the heat-shrinkable film side. A roller was passed over the materials again to ensure proper lamination. The liner was removed from the 1-$cm^2$ piece of double coated tape, and then the stack was laminated into the center of the 2-inch×3-inch (51-mm×76-mm) glass slide with the 467MP lined transfer adhesive being the top layer. A roller was again passed over the sample to ensure proper lamination of all the layers. A permanent marker was then used to outline the original dimensions of the stack and was used as a reference to measure the degree of shrinkage after EO exposure.

The liner on the 467MP transfer adhesive was then removed to expose the adhesive and allow the acid-functional porous sorbent of PE-2 to be bonded to the stack by pouring the acid-functional sorbent over the exposed adhesive. To ensure good adhesion of the acid-functional sorbent, a piece of computer paper was placed over the entire sensor, and a rubber roller was used to lightly press the sorbent particles into the adhesive taking care to not crush the sorbent particles or break the glass slide. The acid-functional porous sorbent of PE-2 loading for sensor CE-2 was 287 $g/m^2$ (gsm).

The sensor CE-2 was exposed to EO using the EO Sterilization Test described above. The response of the sensor CE-2, measured as a percentage of shrinkage of the heat-shrinkable film, is summarized in TABLE 2.

TABLE 2

List of examples, their loadings and responses to EO sterilization conditions.

| Example | Sorbent | Sorbent Loading (gsm) | Acid Concentration (meq/m$^2$) | X-axis Shrinkage (%) | Y-axis Shrinkage (%) | Total Area Shrinkage (%) |
|---|---|---|---|---|---|---|
| EX-1 | PE-1 | 41 | 99 | 8.3 | 12.5 | 19.8 |
| EX-2 | PE-1 | 41 | 99 | 12.5 | 12.5 | 23.4 |
| EX-3 | PE-1 | 59 | 142 | 12.5 | 12.5 | 23.4 |
| EX-4 | PE-1 | 83 | 200 | 50.0 | 45.8 | 72.9 |
| EX-5 | PE-1 | 86 | 207 | 45.8 | 50.0 | 72.9 |
| EX-6 | PE-1 | 107 | 258 | 50.0 | 54.2 | 77.1 |
| EX-7 | PE-1 | 126 | 304 | 54.2 | 58.3 | 80.9 |
| EX-8 | PE-1 | 188 | 453 | 75.0 | 75.0 | 93.8 |
| EX-9 | AMBERLYST 15H | 47 | 221 | 66.7 | 66.7 | 88.9 |
| EX-10 | AMBERLYST 15H | 58 | 273 | 66.7 | 66.7 | 88.9 |
| EX-11 | AMBERLYST 15H | 326 | 1532 | 70.8 | 75.0 | 92.7 |
| EX-12 | PICATOX AMHS37 | 154 | 779 | 66.7 | 66.7 | 88.9 |
| EX-13 | PICATOX AMHS37 | 343 | 1734 | 50.0 | 50.0 | 75.0 |
| CE-1 | — | — | — | 4.2 | 4.2 | 8.2 |
| CE-2 | PE-2 | 287 | 832 | 4.2 | 4.2 | 8.2 |

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An ethylene oxide sterilization sensor comprising:
   a heat-shrinkable film;
   an acid-functional porous sorbent in thermal contact with the heat-shrinkable film; and
   an acid having a boiling point above 120° C. and a pKa of no greater than 2.5, wherein the acid is impregnated in or covalently attached to the porous sorbent.

2. The sterilization sensor of claim 1 wherein the heat-shrinkable film comprises a physically and/or chemically crosslinked polymer.

3. The sterilization sensor of claim 2 wherein the heat-shrinkable film comprises a thermoplastic polyurethane elastomer, a polyurethane with polystyrene and poly(1,4-butadiene) blocks, an ABA tri-block copolymer of poly(tetrahydrofuran) and poly(2-methyl-2-oxazoline), a polyhedral oligomeric silsesquioxane-modified polynorbornene, a polyethylene/Nylon-6 graft copolymer, a polyethylene, a copolymer of ethylene and vinyl acetate, a polyurethane, a polynorbornene, a polyether, a polyacrylate, a polyamide, a polysiloxane, a polyether amide, a polyether ester, a trans-polyisoprene, a polymethyl methacrylate, a polyoctylene, a polycyclooctenes, an inorganic-organic hybrid polymer, a copolymer blend of polyethylene and a styrene-butadiene copolymer, a urethane-butadiene copolymer, a polymethyl methacrylate, a polycaprolactone, an oligocaprolactone copolymer, and combinations thereof.

4. The sterilization sensor of claim 1 wherein the acid-functional porous sorbent comprises activated carbon, porous silica, zeolites, porous organic polymer, or combinations thereof.

5. The sterilization sensor of claim 1 wherein the acid comprises acid moieties covalently attached to the porous sorbent.

6. The sterilization sensor of claim 5 wherein the acid comprises covalently attached acid moieties selected from sulfonic acid (—SO$_3$H) groups and phosphonic acid (—PO$_3$H$_2$) groups.

7. The sterilization sensor of claim 5 wherein the acid is present in an amount of 0.2 mmole to 5.5 mmole of acid moieties per gram of acid-functional porous sorbent.

8. The sterilization sensor of claim 1 wherein the acid comprises acid compounds impregnated within the porous sorbent.

9. The sterilization sensor of claim 8 wherein the acid is selected from acid compounds comprising sulfuric acid, phosphoric acid, methanesulfonic acid, methanephosphonic acid, benzene sulfonic acid, toluene sulfonic acid, or a combination thereof.

10. The sterilization sensor of claim 8 wherein the acid is present in an amount of 5 wt-% to 80 wt-%, based on the total weight of the acid-functional porous sorbent.

11. The sterilization sensor of claim 1 wherein the acid-functional porous sorbent is adhered to the heat-shrinkable film.

12. An array comprising a plurality of the ethylene oxide sterilization sensors of claim 1.

* * * * *